United States Patent [19]
Wiseman

[11] Patent Number: 5,467,782
[45] Date of Patent: Nov. 21, 1995

[54] PATIENT SUPPORT DEVICE

[75] Inventor: Jay Wiseman, Royal Oak, Mich.

[73] Assignee: R-Made, Inc., Bloomfield, Mich.

[21] Appl. No.: 156,680

[22] Filed: Nov. 22, 1993

Related U.S. Application Data

[63] Continuation of Ser. No. 944,361, Sep. 14, 1992, abandoned.

[51] Int. Cl.⁶ ............................................ A61G 15/00
[52] U.S. Cl. .............................. 128/845; 5/636; 5/646
[58] Field of Search .................... D6/595, 596, 601; 297/397, 464; 128/845, 846; 5/632, 636, 643, 646

[56] References Cited

U.S. PATENT DOCUMENTS

| | | | |
|---|---|---|---|
| D. 177,472 | 4/1956 | Huntington | 5/636 |
| D. 308,786 | 6/1990 | Draskovic | D6/601 |
| 2,940,087 | 6/1960 | Kiefer | 5/643 |
| 3,139,631 | 7/1964 | Kiefer | 5/643 |
| 3,195,953 | 7/1965 | Zacks | 297/397 |
| 3,226,159 | 12/1965 | Binding | 297/397 |
| 3,512,605 | 5/1970 | McCorkle | 297/397 |
| 3,606,885 | 9/1971 | Lund | 128/870 |
| 4,154,478 | 5/1979 | Cohune | 297/397 |
| 4,392,489 | 7/1983 | Wagner | 602/24 |
| 4,433,678 | 2/1984 | Spann | 602/24 |
| 4,579,111 | 4/1986 | Ledesma | 5/632 |
| 4,698,837 | 10/1987 | Van Steenburg | 378/208 |
| 5,090,044 | 2/1992 | Kobayashi | 378/208 |

Primary Examiner—Michael A. Brown
Attorney, Agent, or Firm—Gifford, Krass, Groh, Sprinkle, Patmore, Anderson & Citkowski

[57] ABSTRACT

A device for supporting and positioning the arms of a patient lying in a supine position and being subjected to various medical procedures. The device comprises a flat, head-receiving base configured to rest upon a flat surface and having opposed side edges which taper toward each other from bottom to top. A pair of opposed side panels are integrally formed along the side edges and angularly project with respect to the base. The side panels are configured to receive and support the patient's arms when the arms are positioned in an upraised position.

14 Claims, 3 Drawing Sheets

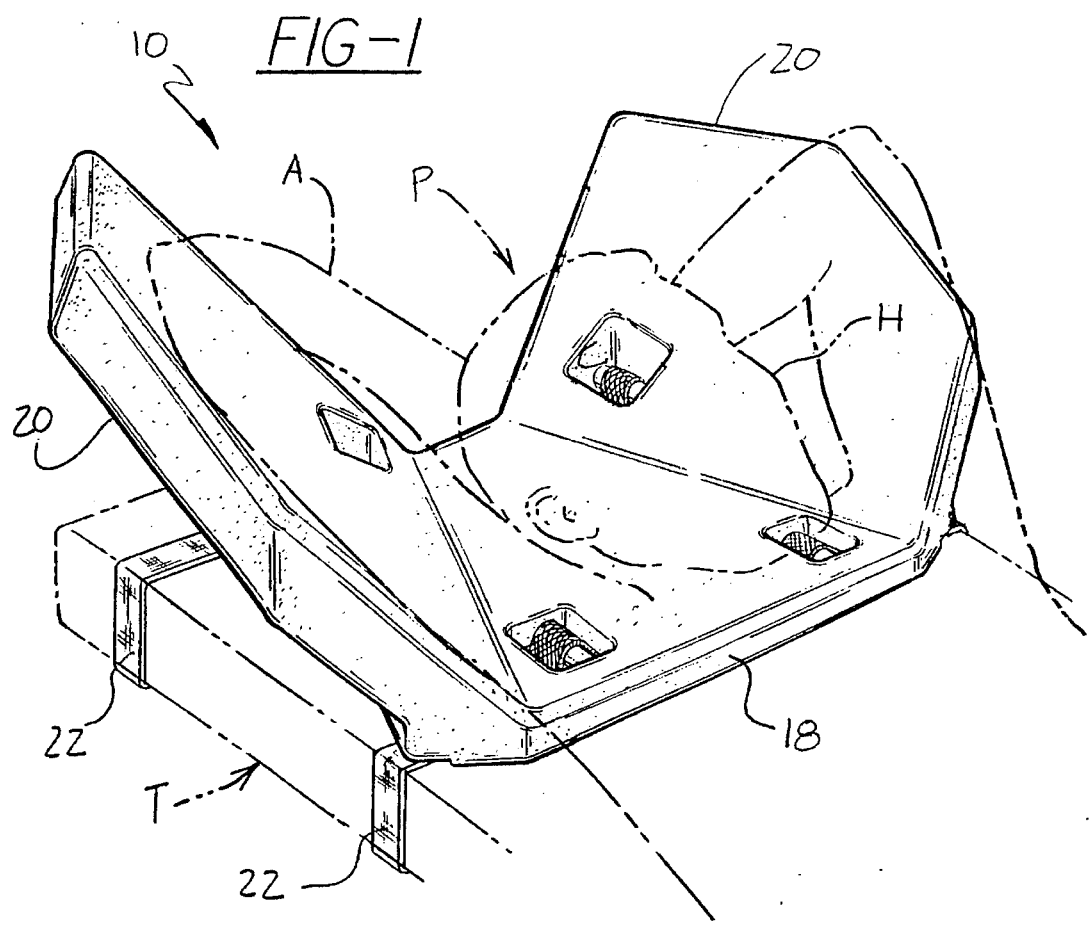
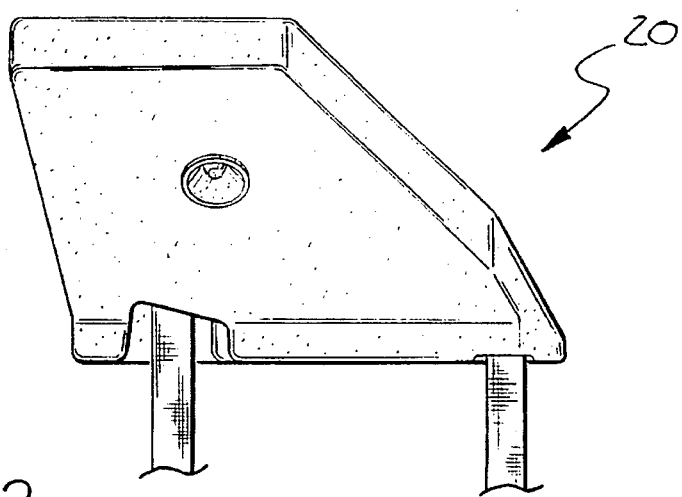

PATIENT SUPPORT DEVICE

This is a continuation of application Ser. No. 07/944,361 filed on Sep. 14, 1992, abandoned.

FIELD OF THE INVENTION

This invention relates to the field of positioning aids for patients and, more particularly, to such an aid for maintaining upraised the arms of a patient who is lying in a supine position as required by certain medical procedures.

BACKGROUND OF THE INVENTION

There are a number of medical and diagnostic procedures, such as angiography, CAT scans, various x-rays, thallium-201 imaging scans, cardiac catheterization, nuclear medicine procedures, etc. which require the patient to remain relatively immobile, in a supine position, with the arms upraised behind the head so that they will not obstruct the studies being done. Of course, it is difficult for a supine patient lying on a flat table such an x-ray table to keep his/her arms upraised in the desired position for a prolonged period of time without shifting or moving them. Yet, some of the procedures requiring this positioning take a minimum of 20 to 30 minutes, or even longer, to complete. Studies done of patients undergoing thallium-201 myocardial SPECT imaging, for example, have shown that patient movement is a serious and common problem which has been recognized in the literature as a significant source of artifactual defects on tomographic reconstructions. It has even been proposed to compensate for patient movements during such thallium studies by shifting the images spatially (pixel by pixel) according to the degree of shift observed on the summated point source image. See, for example, "Patient Motion in Thallium-201 Myocardial SPECT Imaging: An Easy Identified Frequent Source of Artifactual Defect," Friedman J., Berman D. S., Van Train K, et al, *Chemical Nuclear Medicine* 1988:13: 321–4; "Effect of Patient Motion on Tomographic Myocardial Perfusion Imaging," Cooper J., Neuman P., and McCandless B., *Journal of Nuclear Medicine* 1992: 8:1566–1571, and "Sensitivity of SPECT Thallium-201 Myocardial Perfusion Imaging to Patient Motion," Eisner R., *Journal of Nuclear Medicine* 1992: 8:1571–1575 for discussion of the problem and proposed solutions.

While various arm cradles have been improvised to hold the arms during those procedures, they have proved awkward and unsatisfactory in use. For example, Siemen Corporation markets a product known as a "Cath Cradle" which is used to restrain a patient's arms above the head; however, it permanently mounts to a Siemen table and does not have universal applicability.

Of course, other various medical restraints and patient supports are known in the prior art for positioning patients while they are being subjected to various medical procedures. U.S. Pat. Nos.: 4,045,678; 4,156,145; 4,698,837; 4,669,106; and 5,090,044 illustrate such devices. Furthermore, U.S. Pat. No. 4,581,754 discloses an M-shaped positioning device suitable in veterinary applications for restraining animals during radiographical procedures. While some of the devices disclosed in the above-listed patents are useful for various purposes, none of them are suitable for positioning the upraised arms of a patient lying in a supine position.

Hence, there is a need for a device which positions the arms of a supine patient in an upraised position and supports the arms in that position during prolonged radiographic and other studies. Furthermore, there is a need for such a device which is simple to manufacture, easy to use, and comfortable for the patient, and which can universally be adapted for use with a variety of medical studies without the necessity of otherwise altering the equipment.

SUMMARY OF THE INVENTION

Disclosed and claimed herein is a device for supporting and positioning the arms of a patient who is lying in a supine position during medical procedures such as radiographic studies, thallium studies and angiography. The device comprises a flat, head-receiving base which is configured to rest upon a flat surface, such as an x-ray table. The base has opposed side edges which taper toward each other to define a shorter top edge and a longer bottom edge.

A pair of opposed side panels are integrally formed along each of the side edges of the base. The side panels angularly project outward from the base, preferably at an approximate 120° angle therewith. Each of the side panels is configured to receive one of the arms of the patient when the arm is upraised above and behind the patient's head. Each side panel is preferably configured as a square shape, the square having a truncated lower, outermost edge.

It will be noted that the side panels angularly project upward and outward with respect to the plane of the base. Moreover, since the side edges of the base taper toward each other in a direction from bottom edge to top edge, the side panels project from the base at a compound angle with respect thereto. For example, if the base is configured as a truncated equilateral triangle (with the top vertex truncated), the side walls panels will incline toward each other at an approximate 60° angle, and also form approximate 120° angles with respect to a horizontal plane. Thus, if the respective planes through which the pair of side panels pass are extended rearwardly of the base, the two side wall planes will intersect. Moreover, if these two planes are extended upward from the top edge of the base, they will also intersect.

In one embodiment of the support device of the present invention, the device is formed of a radiographically-transmissive material. It also is provided with means for attaching it to the flat surface, typically an x-ray table. The means may comprise one or more straps which are threaded through opposed pairs of apertures formed in the base or the side panels of the support device proximate the side edges of the base. By including the straps, the device may simply be strapped to the table to secure it thereto.

In certain medical procedures, it may be necessary for the supine patient to extend his/her upraised arm toward the opposite side of the body. This is particularly true in procedures involving the mammary glands or underarm region. In order to facilitate such positioning, the device of the present invention may be provided with a loop which is attached to each of the side panels proximate a top edge thereof. The patient may then simply grasp the loop attached to the side panel on the opposite side of his/her body; that is, if the procedure involves the right breast and right side of the body, the patient will extend the right arm toward the left side panel of the device and grasp its attached loop. Conversely, if the studies involve the left side, the patient will extend the left arm and grasp the loop attached to the right side panel.

Preferably, the device is formed of a polymeric material such as molded high density polyethylene, which is essentially radiographically transparent. In order to help rigidify and strengthen the side panels of the molded device, a thickened portion may be provided which is disposed on an undersurface of each side panel proximate the respective side edge of the base and extending therealong.

BRIEF DESCRIPTION OF THE DRAWINGS

The following detailed description may best be understood by reference to the following drawings in which:

FIG. 1 is a perspective view of a device according to the present invention strapped to a flat surface, showing the use thereof by a patient shown in phantom lines;

FIG. 2 is a right side elevational view of the device shown in FIG. 1;

DETAILED DESCRIPTION OF THE PREFERRED EMBODIMENTS

Figure 3:
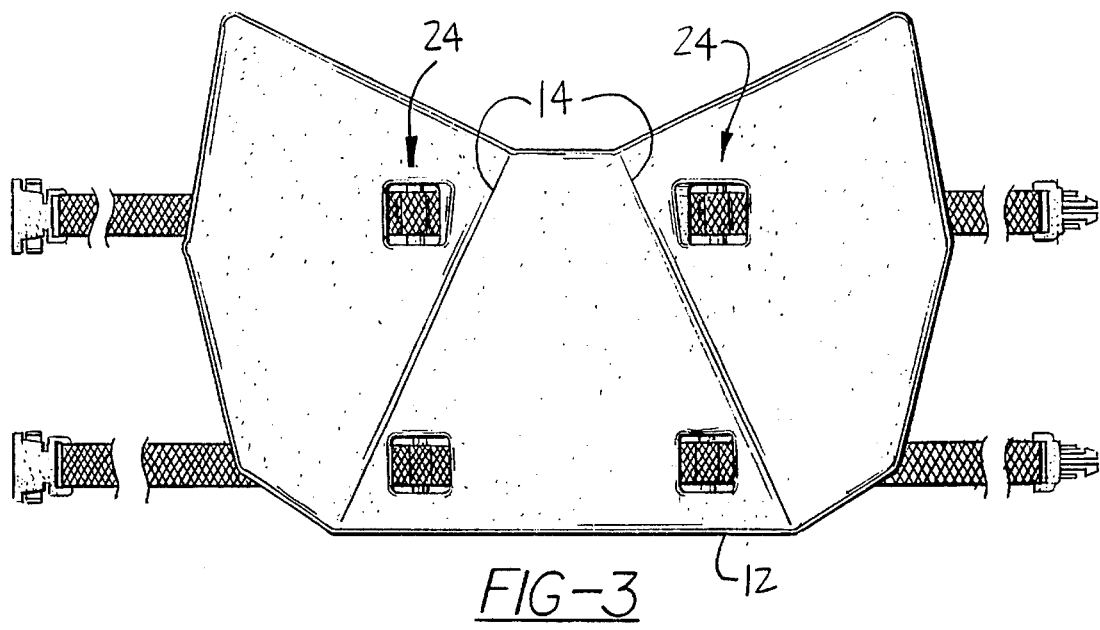
FIG. 3 is a front elevational view of the device of FIG. 1.

Throughout the following detailed description like reference numerals will be used to refer to the same element of the invention shown in multiple figures thereof. Referring now to the drawings, and in particular FIGS. 1 and 3, there is shown a support device 10 for use in various medical procedures where it is necessary to support the arms A of a supine patient P in an upraised position. By "upraised," the inventor means that the patient's arms are raised so that they are disposed proximate the head. Since the patient is also lying supine, the "upraised" arms will actually be oriented generally in a horizontal plane. The device 10 comprises a flat base 12 configured to rest upon a flat surface such as table T. In the illustrated embodiments, the flat base 12 is in the approximate shape of a truncated equilateral or isosceles triangle, although it may have a variety of other suitable shapes.

Figure 7:
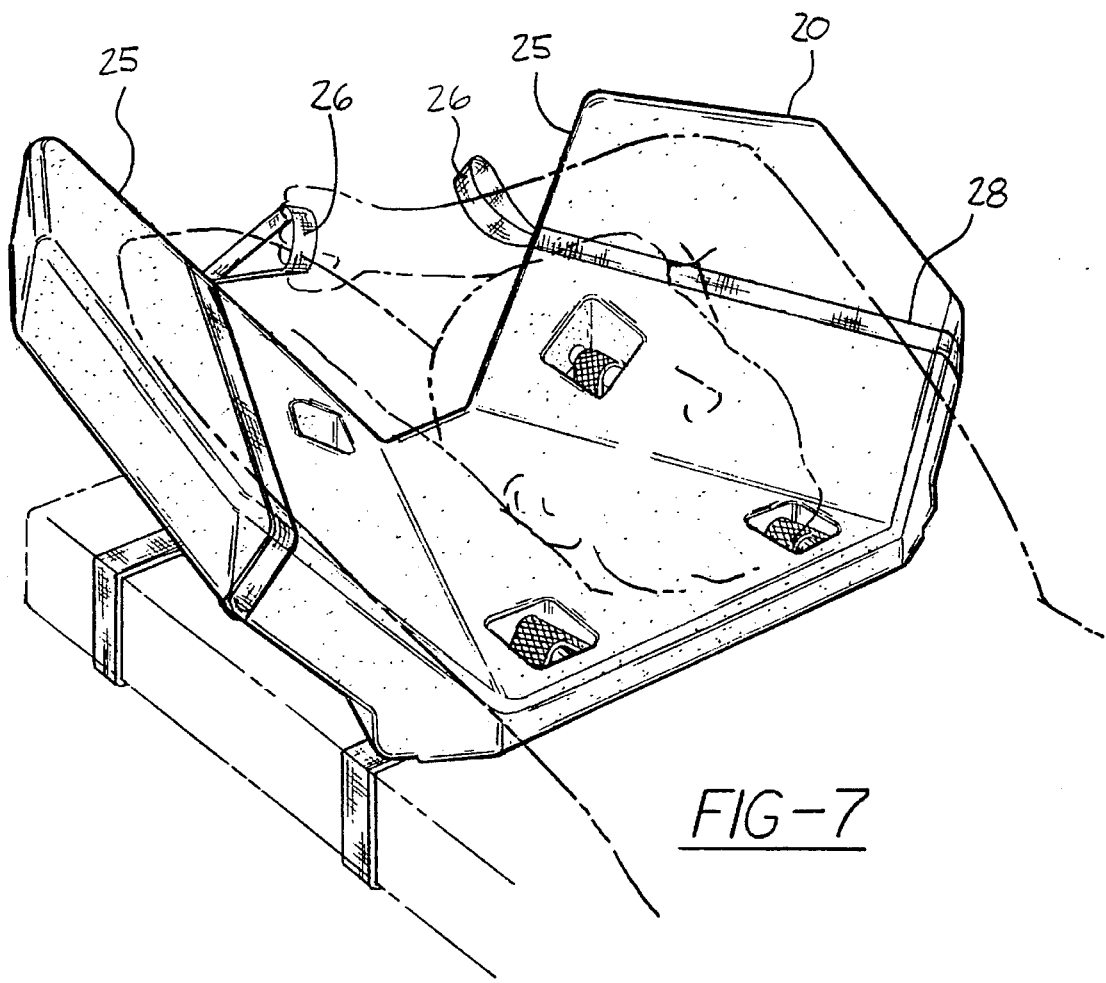
FIG. 7 is an alternate embodiment of the device of the present invention showing the use of certain additional features thereof by a patient shown in phantom lines.

The side edges 14 of flat base 12 taper toward each other to define a longer, bottom edge 18 and a shorter top edge 16. As can be seen in FIGS. 1 and 7, the patient P uses the device by lying with his/her head H on flat base 12, with the remainder of the body extending down from the bottom edge 18.

A pair of opposed side panels outwardly project from flat base 12 to form an angle A therebetween. In practice, it has been found that if angle A is chosen to be approximately 120°, side panels 20 will form comfortable rests for the patient's arms. The side panels 20 are integrally formed on side edges 14 of flat base 12 and, due to the taper of side edges 14, project from flat base 12 at a compound angle with respect thereto. It has been found that this compound angle is necessary to provide a comfortable resting surface for the patient's arms.

As can be seen in FIG. 1, the patient P is positioned so that the head H lies on flat base 12 and each arm A rests upon its respective side panel 20. Most typically, the patient will bend the arm at the elbow inwardly and rest his/her hands above his head, either on the flat base 12 or the table T. In actual usage, it has been found that patients readily accept such positioning, and are able to maintain their arms in the comfortable, resting position provided by the device of the present invention for extended periods of time.

Figure 4:
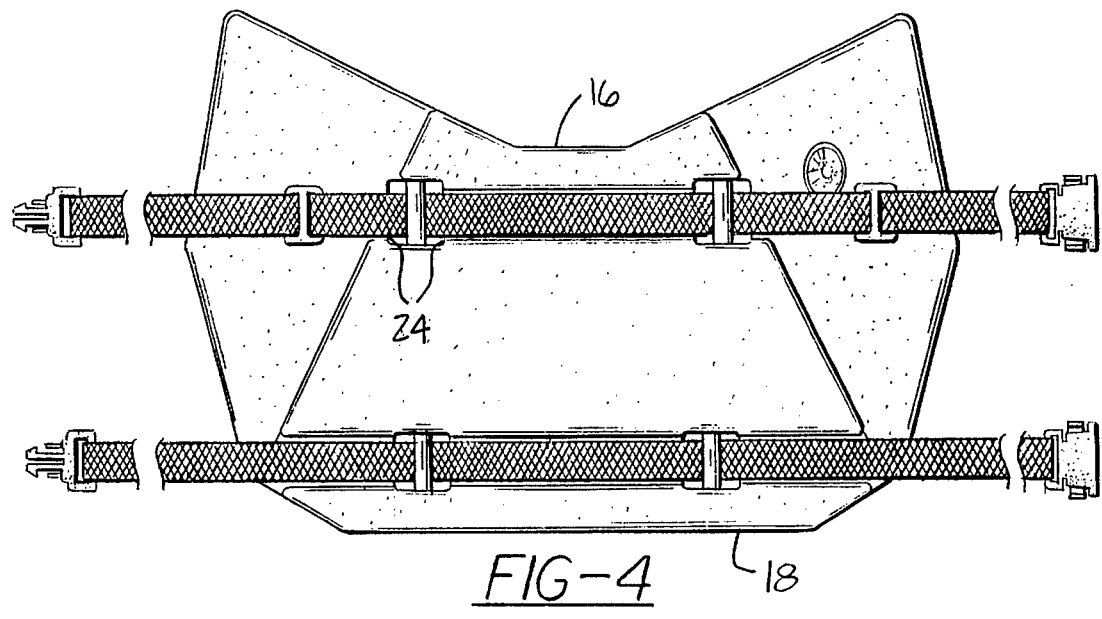
FIG. 4 is a rear elevational view of the device of FIG. 1.
Figure 5:
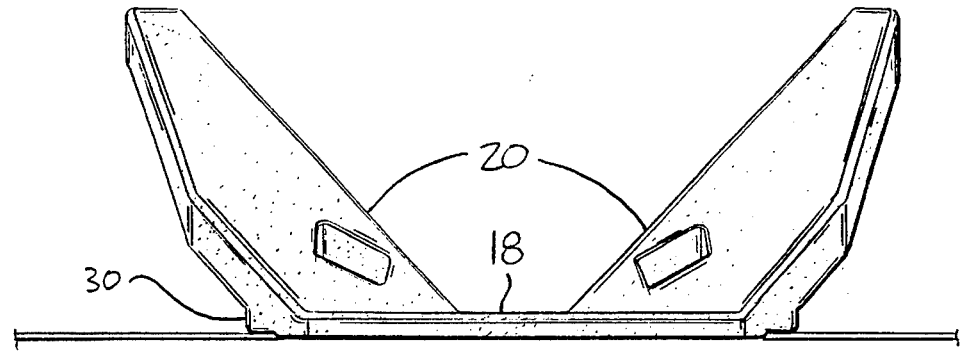
FIG. 5 is a bottom view of the device of FIG. 1.
Figure 6:
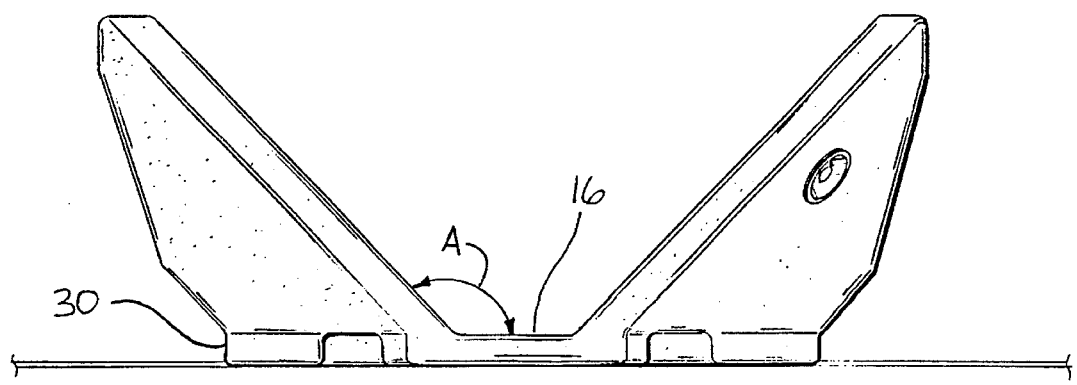
FIG. 6 is a top plan view of the device of FIG. 1.

As can be most clearly seen in FIG. 4, the device of the present invention may further be provided with universal mounting means for attaching it to a table such as table T. The means are in the form of a pair of straps 22 which are threaded through pairs of opposed apertures 24 formed in either or both the side panels 20 and base 12 in the manner shown in FIGS. 3 and 4. A pair of straps 22 provides the most reliable and secure attachment. Since, typically, the device of the present invention is formed by blow molding, the pairs of apertures 24 may be simply molded into the device.

Preferably, the device is formed of a radiographically-transmissive, easily-molded material such as high density polyethylene, polypropylene, acrylic, polystyrene, polycarbonate, latex rubber, fiberglass, etc. The device can even be formed of a cast resin strengthened with carbonic fibrous material, such as is described in U.S. Pat. No. 4,146,793. All of these materials provide comfortable, impervious and easily cleanable surfaces. In order to further strengthen the device of the present invention at the point where the side panels 20 angularly project from the base 12, a thickened portion 30 may be formed on each side panel 20 at a rear surface thereof proximate its juncture with base 12 at side edge 14 and extending along the length thereof.

An alternate embodiment of the device of the present invention is shown in FIG. 7. It is identical to the embodiment shown in FIGS. 1–6 except that it has the additional feature of loops 26 which are attached to either, or both, side panels 20 at a top edge 25 thereof. An easy way of attaching the loop 26 is simply by extending a strap 28 around the entire width of the side panel 20, as is shown in FIG. 7. The purpose of the loops 26 are to provide a grasp for the patient when it is necessary for him/her to cross one of his/her arms to the other side of the body. Such a cross-over position may be necessary for certain medical studies involving the mammary glands and underarm region. The embodiment of the device of the present invention shown in FIG. 7 particularly facilitates such positioning. In the drawing of FIG. 7, the patient is shown with her left hand grasping the loop 26 of the right panel 20.

From the above description, it can be seen that the device of the present invention provides a simple, inexpensive and practical solution to the problem of patient motion during prolonged medical procedures where the patient is required to raise his/her arms above and behind the head. The device can be used with a variety of medical equipment and does not interfere with any of the instrumentation associated therewith. Unlike prior art approaches, it does not require expensive redesign or reprogramming of the diagnostic devices. If necessary, the device can be fabricated in two or more sizes to accommodate a wider range of patients. However, in practical use, it has been found that a device having external dimensions of approximately 22×12×8.5 inches will accommodate most patients. A device having approximately these external dimensions will have an base flat inside surface measurement of about 11½ inches at the longer edge tapering to 3 inches at the smaller end, with side edges of 11 inches. The side panels will measure approximately 10×11 inches, with a 4.75×4.75×6.75 inch triangular corner cut-away. When the device is fabricated of blow molded polyethylene, it weighs less than three pounds.

The present invention has been described with reference to certain embodiments and exemplifications thereof. Certain variations and modifications of the embodiments depicted may occur to one skilled in the art by utilizing the teachings of the present invention. However, such modifications and variations are considered to fall within the scope of the claims of the present invention. It is these claims, rather than the embodiments and exemplifications described herein, which define the scope of the invention.

I claim:

1. A device for supporting, positioning and elevating the forearms of a patient lying in a supine position such that at least one of the patient's hands may be positioned behind the patient's head during a medical procedure, said device comprising:

a flat, head-receiving base dimensioned to receive a patient's head thereupon and configured to rest upon a flat surface, said base defining a plane and having opposed side edges which taper toward each other to define a shorter top edge and a longer bottom edge;

a pair of opposed, planar, side panels integrally formed along each of said side edges and angularly projecting upward and outward from the plane defined by said base, said planar side panels being dimensioned and configured to receive said patient's forearms when said forearms are positioned proximate said patient's head such that said forearms project out of the plane of the base.

2. The device of claim 1 further comprising means for securing said device to said flat surface.

3. The device of claim 2 wherein said means for securing further comprises at least one strap attached to said device.

4. The device of claim 3 wherein said device further comprises means forming two opposed pairs of apertures disposed proximate said side edges, said straps being attached to said device by sequentially threading said strap in and out of said apertures.

5. The device of claim 1 wherein the device is formed of a radiographic transmissive material.

6. The device of claim 1 further comprising a loop attached to one of said side panels proximate a top edge thereof such that said loop may be grasped by the hand of the arm supported on the opposite side panel when patient reaches across his body.

7. The device of claim 1 further comprising a thickened reinforcement portion formed on an undersurface of each side panel proximate said side edge of said base and extending therealong.

8. The device of claim 1 wherein each side panel is configured as a square having a lower, outermost, truncated corner.

9. The device of claim 1 wherein said flat base is configured as a trapezoid.

10. The device of claim 8 wherein the flat base has a width of approximately 11¼ inches at the bottom edge and 3 inches at the top edge, with side edges each approximately 11¼ inches long, and the side panels each have a width of approximately 10 inches, a height of approximately 11 inches, said truncated corner having dimensions of approximately 4¾×4¾×6¾ inches.

11. The device of claim 1 wherein each of said side panels defines a plane, said side panels angularly projecting upward and outward from said base such that said side panel planes intersect along a first line displaced outboard from said top edge of said flat base, and along a second line rearwardly displaced from said flat base.

12. The device of claim 11 wherein said side panel planes form an approximate 60° angle along said first line and an approximate 60° angle along said second line.

13. A device for supporting, positioning and elevating the forearms of a patient lying in a supine position such that at least one of the patient's hands may be positioned behind the patient's head during a medical procedure, said device comprising:

a flat, head-receiving base dimensioned to receive a patient's head thereupon and configured to rest upon a flat surface, said base having opposed side edges which taper toward each other to define a shorter top edge and a longer bottom edge;

a pair of opposed, planar, side panels integrally formed along each of said side edges and angularly projecting upward and outward from said base, said planar panels being dimensioned and configured to receive said patient's forearms when said forearms are positioned proximate said patient's head such that at least one of said patient's hands are free to rest on said base behind the head; and a loop attached to one of said side panels proximate a top edge thereof such that said loop may be grasped by the hand of the forearm supported on the opposite side panel when the patient reaches across his body.

14. A device for supporting, positioning and elevating the forearms of a patient lying in a supine position such that at least one of the patient's hands may be positioned behind the patient's head during a medical procedure, said device comprising:

a flat, head-receiving base dimensioned to receive a patient's head thereupon and configured to rest upon a flat surface, said base being configured as a trapezoid having opposed side edges which taper toward each other to define a shorter top edge and a longer bottom edge, said flat base having a width of approximately 11¼ inches at the bottom edge and three inches at the top edge, with side edges each approximately 11¼ inches long; and a pair of opposed, planar, side panels integrally formed along each of said side edges and angularly projecting upward and outward from said base, said side panels each having a width of approximately 10 inches, a height of approximately 11 inches, and a lower, outermost truncated corner having dimensions of approximately 4¾×4¾×6¾ inches, said planar panels being configured to receive said patient's forearms when said forearms are positioned proximate said patient's head such that at least one of said patient's hands are free to rest on said base behind the head.

* * * * *